(12) United States Patent
Kay

(10) Patent No.: US 7,833,225 B2
(45) Date of Patent: Nov. 16, 2010

(54) METHOD AND DEVICE FOR BONE STABILIZATION USING A THREADED COMPRESSION WIRE

(75) Inventor: David B. Kay, Akron, OH (US)

(73) Assignee: Orthohelix Surgical Designs, Inc., Medina, OH (US)

( * ) Notice: Subject to any disclaimer, the term of this patent is extended or adjusted under 35 U.S.C. 154(b) by 1331 days.

(21) Appl. No.: 10/831,586

(22) Filed: Apr. 23, 2004

(65) Prior Publication Data

US 2005/0043734 A1   Feb. 24, 2005

Related U.S. Application Data

(60) Provisional application No. 60/465,187, filed on Apr. 24, 2003.

(51) Int. Cl.
*A61B 17/82* (2006.01)

(52) U.S. Cl. ...................................... 606/60

(58) Field of Classification Search ............... 606/60, 606/74, 103, 300, 301, 303, 86 R, 151, 232, 606/228, 144, 148; 140/93.2, 93.4, 105, 140/106
See application file for complete search history.

(56) References Cited

U.S. PATENT DOCUMENTS

| | | | |
|---|---|---|---|
| 2,143,922 A * | 1/1939 | Longfellow | 606/60 |
| 5,163,960 A | 11/1992 | Bonutti | |
| 5,370,646 A | 12/1994 | Reese et al. | |
| 5,609,595 A | 3/1997 | Pennig | |
| 5,611,801 A * | 3/1997 | Songer | 606/308 |
| 5,628,752 A | 5/1997 | Asnis et al. | |
| 5,709,687 A | 1/1998 | Pennig | |
| 5,720,747 A * | 2/1998 | Burke | 606/74 |
| 5,868,748 A * | 2/1999 | Burke | 606/74 |
| 5,997,542 A * | 12/1999 | Burke | 606/74 |
| 6,050,998 A * | 4/2000 | Fletcher | 606/74 |
| 6,068,648 A | 5/2000 | Cole et al. | |
| 6,368,326 B1 * | 4/2002 | Dakin et al. | 606/103 |
| 6,576,018 B1 * | 6/2003 | Holt | 623/21.11 |
| 6,638,279 B2 * | 10/2003 | Bonutti | 606/60 |
| 6,761,722 B2 * | 7/2004 | Cole et al. | 606/74 |
| 2002/0091391 A1 * | 7/2002 | Cole et al. | 606/72 |

FOREIGN PATENT DOCUMENTS

WO    WO 9811838 A1 *  3/1998

* cited by examiner

*Primary Examiner*—Eduardo C Robert
*Assistant Examiner*—David Comstock
(74) *Attorney, Agent, or Firm*—Hudak, Shunk & Farine Co. LPA

(57) ABSTRACT

A partially threaded compression wire with a trocar insertion point is inserted into a first bone fragment and a mating button is crimped into position on the wire to cause compression between the first bone fragment and a second bone fragment. A cannulated instrument applies tension to the wire and crimps the button. In a second embodiment, the wire further includes an internally threaded screw or helix. In the related method, the threaded wire is implanted ante grade or retrograde into the first bone segment and a button is crimped to the wire to apply compression to a second bone segment either cutaneously or percutaneously.

2 Claims, 3 Drawing Sheets

METHOD AND DEVICE FOR BONE STABILIZATION USING A THREADED COMPRESSION WIRE

THIS PATENT APPLICATION IS BASED UPON U.S. PROVISIONAL APPLICATION SER. NO. 60/465,187 FILED Apr. 24, 2003

The present invention relates to a compression wire for use in bone fixation where the wire is partially threaded and has a trocar insertion point. A button mates with the wire and can be crimped into position to cause compression. A cannulated instrument is used to grasp and apply tension to the wire at a given torque, and further to crimp the button to maintain tension on the wire in a location suitable for later removal. In a second embodiment for osteoporotic bone the wire further includes an internally threaded screw or helix implant which mates with the threads of the wire. The invention further relates to the method of fixation in which the threaded wire is implanted into the distil end of a bone segment in ante grade or retro grade fashion, the protruding end subsequently receives a button slid onto the wire so that it abuts near the bone segment. The end of the wire assembly may be left proud for later removal, or countersunk in the bone so as not to protrude. A cannulated instrument is used to perform the tensioning/crimping technique. The invention is particularly useful for small bone fractures, i.e. in the wrist, hand, ankle or foot.

BACKGROUND OF THE INVENTION

Bone stabilization is the hallmark of modern orthopedic fracture care and reconstruction and involves stabilization of a break or fracture in order to allow the bone fragments to knit. Standard stabilization devices include plates, wires, and screws. Plates tend to be rigid and their uses are generally limited due to space requirements to long bone breaks or fractures. Wires may be stiff or flexible depending upon application. Screws are of metal or bioabsorbable materials and are of varying size and pitch. Cannulated screws have a central through-hole, so that they can be positioned accurately using minimal incision principals. Small wire external fixators, such as the Ilizarov, apply tension to a wire that is placed through the bone. These devices can include percutaneous application in which a portion of the implant remains outside the incision. Tensioned wire is better able to resist bending forces, than a wire in compression, and can be used to apply compression to bone segments when a live "wire" is utilized. The application of compression also has physiological effects on the bone being stabilized and can promote faster bone growth and/or better healing.

One of the prior art techniques is known as an olive wire, which has a metallic enlargement that abuts the bone. Tension is applied to the wire and maintained by a bolt and washer system that is applied to a frame external to the incision.

SUMMARY OF THE INVENTION

The present invention is intended to integrate some of the noted principles in a novel way. The concept is to use a partially threaded wire that has a sharp trocar point on an opposing end which is fixed in a bone in ante grade or retrograde fashion in order to attach two or more bone segments. The threaded end is kept in the distal or far bone segment to anchor that segment and to enable the compression between the segments. The wire is inserted through both bone segments and put into compression in order to adjoin the segments under a measured tension. The tension is maintained by a button which abuts a bone segment holding the non-threaded portion of the wire. The wire is crimped in the button to maintain the compression.

In a second embodiment, a helix may be used to augment the purchase such as in bone of poor quality. The helix is implanted into a bone segment and the wire is threaded into the helix. As for the first embodiment, a wire guide is used for the insertion of the wire and a cannulated instrument is used to grasp the protruding wire. A crimp-tension and cutting tool is used to secure the button on the wire and to cause the compression. The button may be countersunk in the bone, or may remain at the surface of the bone, or may even reside above the skin after closure, i.e. proud.

DETAILED DESCRIPTION OF THE INVENTION

Figure 1:
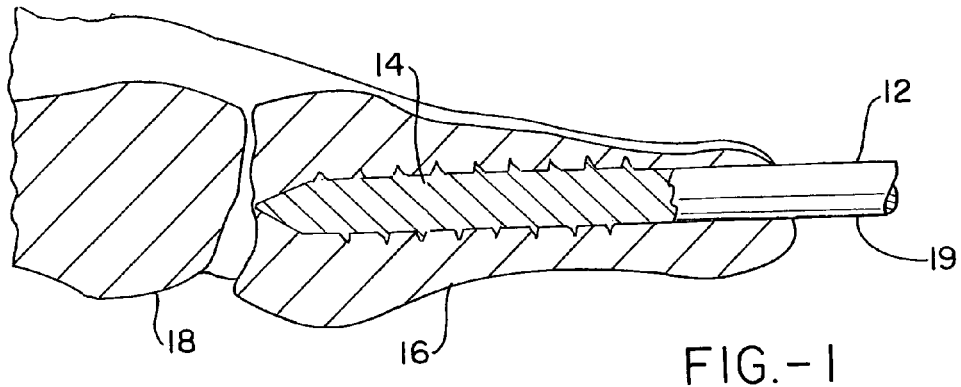
FIG. 1 is a schematic representation of the first step in the standard implantation of the threaded wire in accordance with the present invention.
Figure 2:
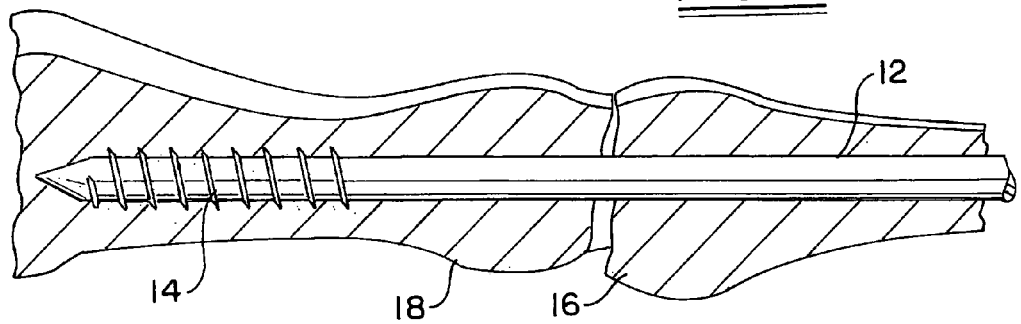
FIG. 2 is a schematic representation of the second step in the standard implantation of the threaded wire.
Figure 3:
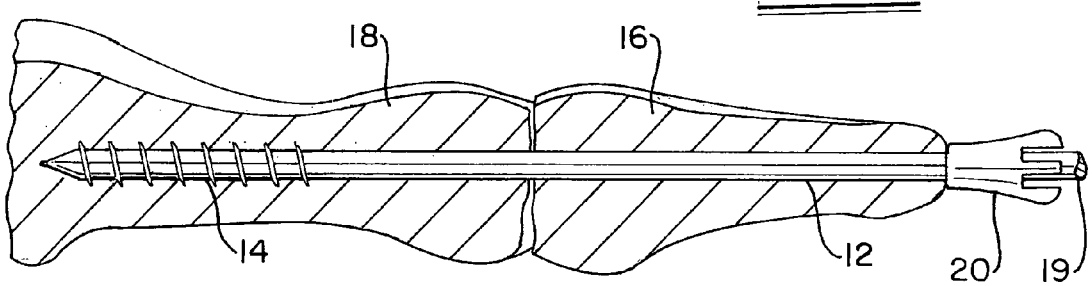
FIG. 3 is a schematic representation of the third step in the standard implantation of the threaded wire in accordance with the present invention.
Figure 4:
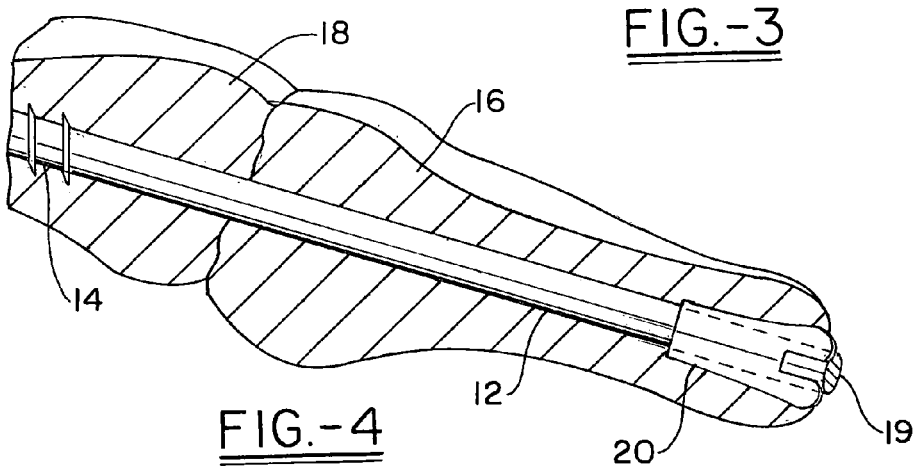
FIG. 4 is a schematic representation of a side view of the button above the bone.

FIGS. 1-4 illustrate a standard technique in accordance with the present invention in which a wire 12 having a threaded end portion 14 is inserted through a first bone segment 16 into a far bone segment 18 where it is screwed in to anchor the second bone segment. A cannulated instrument is used which allows the wire to be implanted through the first bone segment 16 into the second bone segment 18. The wire is tensioned so that the first bone segment slides into the second bone segment and the segments are compressed. An end portion 19 of the wire is left protruding above the surface of the first bone segment 16 to allow access to the wire 12. A button 20 includes a hole that receives the end portion 19 of the wire 12. The button further includes means to crimp the wire into a measured tension in the button. The button is configured so that it applies pressure against the abutting bone surface of the first bone segment 16. The button is crimped to maintain the wire tension and bone compression. A tension gauge can be used in order to assure that the wire is under the proper tension. The crimped button can be left proud (Percutaneous Technique) or buried in the bone.

Figure 5:
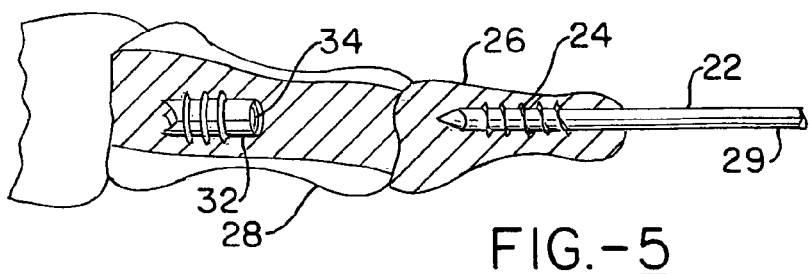
FIG. 5 is a schematic representation of the first step in the direct implantation of the threaded wire in accordance with a second embodiment of the present invention.
Figure 6:
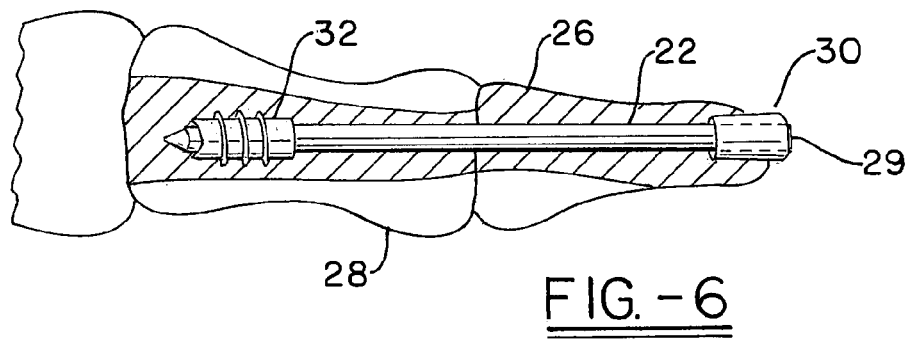
FIG. 6 is a schematic representation of the second step in the direct implantation of the second embodiment of the threaded wire.

In the second embodiment which is illustrated in FIGS. 5 and 6, the external end threads 24 of the wire 22 mate with the internal threads 34 of the a mating anchor 32, such as a screw or a helix or threaded washer. The anchor 32 may be inserted directly through the near bone segment 26 into the far bone segment 28 under direct visualization and the wire is advanced into cooperation with these threads. The wire is retrograded through the distal segment and then passed ante grade into the mating anchor. Once again, after screwing the threads into the far bone segment, the wire is drawn into compression to adjust the location of the segments as desired. The end 29 of the wire is fed through a button 30, adjusted to the proper tension, and crimped into position. Part or all of the technique can be percutaneous, for example, the wire can be inserted directly through the skin, as can the anchor. A mating helix presents unique advantages for use as the anchor, and is thus preferred for certain indications since it would be compressed during the tensioning technique and will maintain the mated wire and the bone segments in compression. The button can be left proud or countersunk. The threads engage and tension is applied to the wire to compress the segments and the button is then crimped. The bone ends will be compressed.

Figure 7:
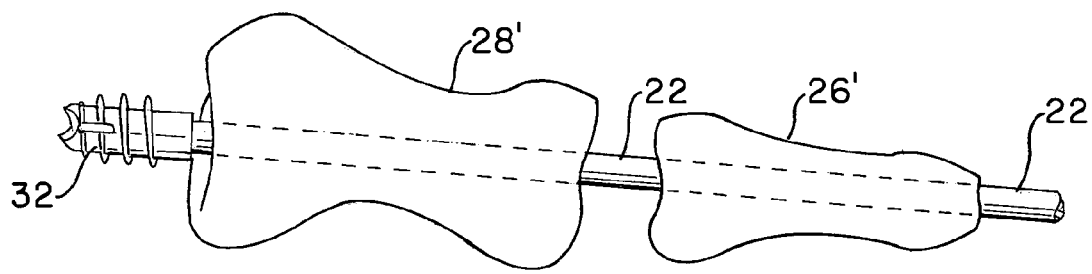
FIG. 7 is a schematic representation of the first step in the retrograde implantation of the threaded wire in accordance with the present invention.
Figure 8:
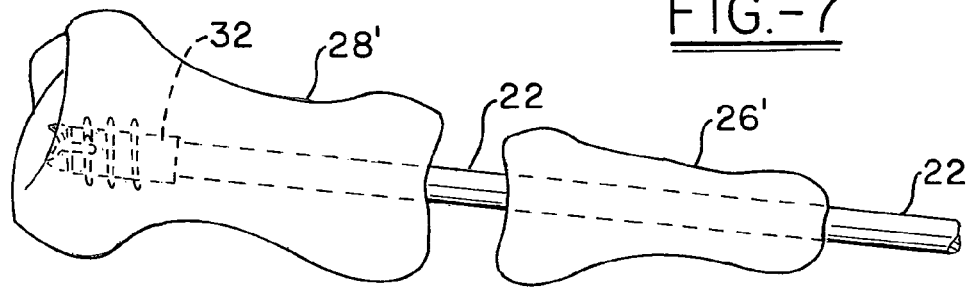
FIG. 8 is a schematic representation of the second step in the retrograde implantation of the threaded wire.
Figure 9:
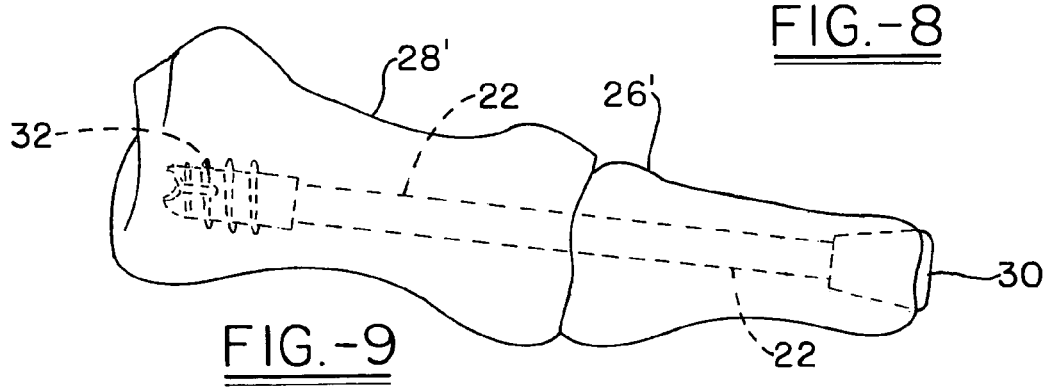
FIG. 9 is a schematic representation of the third step in the retrograde implantation of the threaded wire.

FIGS. 7-9 illustrate a retrograde insertion of the wire and anchor assembly as are shown in the standard technique in FIGS. 5 and 6. In the retrograde insertion, the wire 22 is first threaded into the mating anchor 32 which is implanted into the second segment 28' and into the first bone segment 26' with the wire projecting though it. The bone segments 26' and 28' are brought into proximity so that the wire projects out the other side of the first bone segment and can be fastened in place in the button 30.

Figure 10:
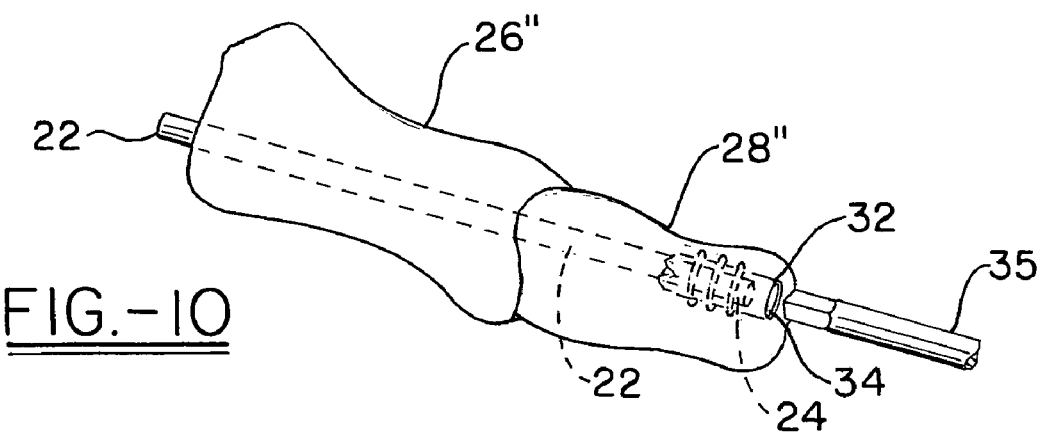
FIG. 10 is a schematic representation of a method of percutaneous implantation of the threaded wire in accordance with the present invention using a cannulated instrument.
Figure 11:
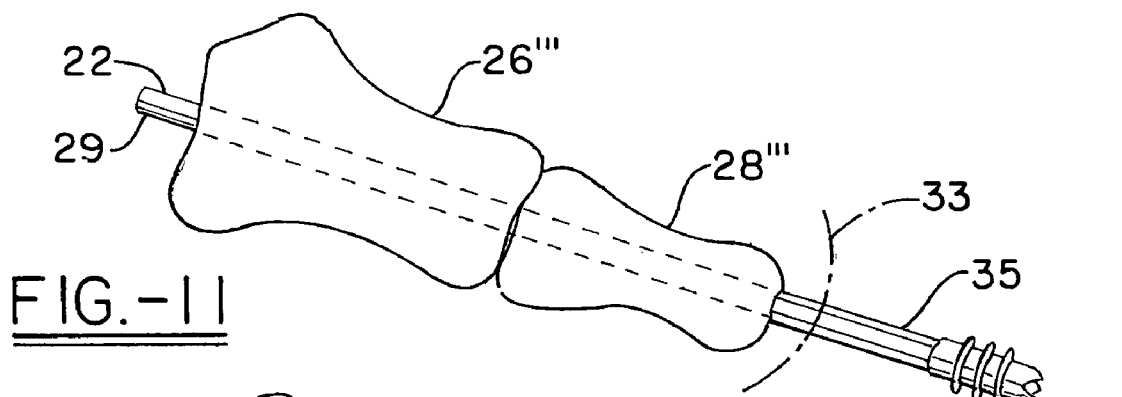
FIG. 11 is a schematic representation of the second method for percutaneous implantation of the threaded wire using a cannulated instrument.
Figure 12:
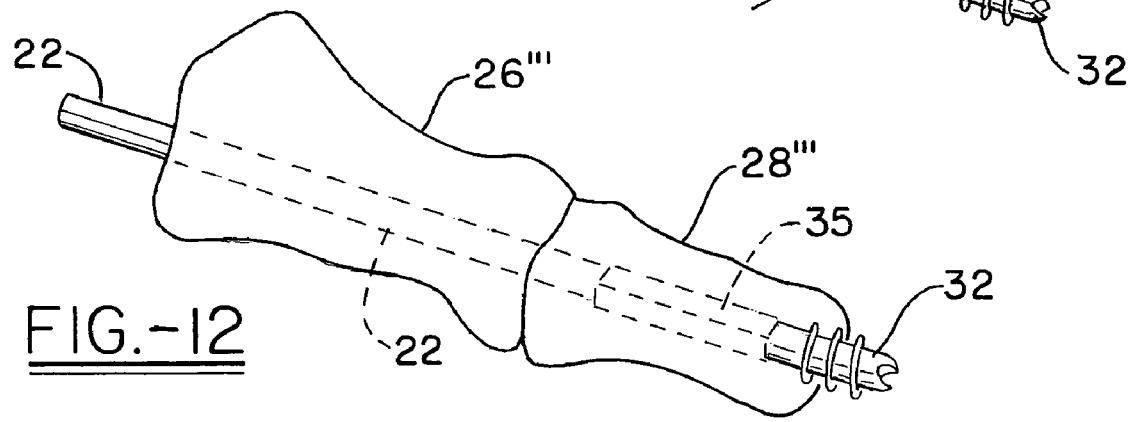
FIG. 12 is a schematic representation of the second step in the percutaneous implantation shown in FIG. 11.
Figure 13:
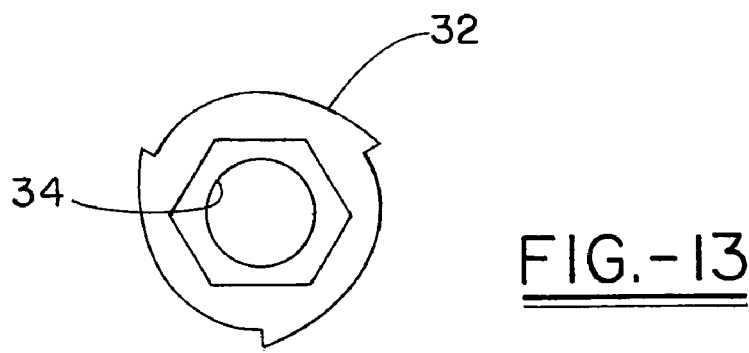
FIG. 13 is a top plan view of the cannulated implantation instrument in accordance with the present invention.

FIGS. 10-13 illustrate a percutaneous and cannulated technique for the insertion of the wire and anchor assembly. In FIG. 10, the wire 22 is first implanted through the first bone segment 26" where it mates with the anchor 32 that has been inserted into the second bone segment 28" using a cannulated instrument 35. The threaded end 24 of the wire 22 is screwed into the internal threads 34 of the anchor 32. In a retrograde method of implantation shown in FIGS. 11 and 12, the wire 22 is first threaded into the anchor 32 which is positioned in the cannulated instrument 35. The anchor 32 along with the instrument 35 are implanted through the skin 33 so that the end of the wire 29 projects beyond the first bone segment 26''' and can be accessed for tensioning with the button (not shown). The instrument 35 and the anchor are left in the second bone segment 28'''. FIG. 13 shows a top plan view of the anchor which includes an internal hexagon and internal threads 34 that will mate with the threads of the wire.

While in accordance with the patent statutes, the best mode and preferred embodiment have been set forth, the scope of the invention is not limited thereto, but rather by the scope of the attached claims.

What is claimed is:

1. A method of stabilization of a bone segment comprising the step of implanting compression assembly comprising a wire which is sufficiently rigid to apply an axial compressive force and which has threads and an insertion point and a button having a distal end and comprising the steps of
   implanting the wire through a first bone segment;
   threading the wire into a second bone segment;
   positioning the bone segments in a desired relationship and under a desired tension; and
   fastening the button about the wire proximal to the threaded portion and crimping the wire in the button such that the distal end of the button applies a force to the first bone segment axial to the wire in order to maintain the wire under the desired tension.

2. A method as set forth in claim 1 wherein the second bone segment is first secured to the first bone segment and then drawn into compression with the first bone segment using the wire.

* * * * *